(12) United States Patent
Chauhan et al.

(10) Patent No.: US 7,790,427 B1
(45) Date of Patent: Sep. 7, 2010

(54) METHOD OF TREATING BIOCELLS

(75) Inventors: Satya P. Chauhan, Columbus, OH (US); Paul J. Usinowicz, Powell, OH (US)

(73) Assignee: Battelle Memorial Institute, Columbus, OH (US)

( * ) Notice: Subject to any disclaimer, the term of this patent is extended or adjusted under 35 U.S.C. 154(b) by 792 days.

(21) Appl. No.: 11/523,171

(22) Filed: Sep. 19, 2006

Related U.S. Application Data

(60) Provisional application No. 60/718,667, filed on Sep. 20, 2005.

(51) Int. Cl.
*C12N 13/00* (2006.01)

(52) U.S. Cl. .................. 435/173.6; 435/173.7; 435/375; 435/383

(58) Field of Classification Search ........................ None
See application file for complete search history.

(56) References Cited

U.S. PATENT DOCUMENTS

| | | | |
|---|---|---|---|
| 4,961,860 A | 10/1990 | Masri | 210/748 |
| 5,380,445 A | 1/1995 | Rivard et al. | 210/748 |
| 5,846,425 A | 12/1998 | Whiteman | 210/606 |
| 5,976,375 A | 11/1999 | Dorica et al. | 210/610 |
| 6,013,183 A | 1/2000 | Stephenson et al. | 210/606 |
| 6,030,538 A | 2/2000 | Held | 210/748 |
| 6,039,867 A | 3/2000 | Frei et al. | 210/173 |
| 6,395,176 B1 | 5/2002 | Held et al. | 210/610 |
| 6,402,065 B1 | 6/2002 | Higgins | 241/21 |
| 6,491,820 B2 | 12/2002 | Held et al. | 210/609 |
| 6,540,919 B2 | 4/2003 | Held et al. | 210/609 |
| 6,635,178 B2 | 10/2003 | Bowman et al. | 210/609 |
| 6,709,594 B2 | 3/2004 | Held et al. | 210/609 |
| 6,780,319 B1 | 8/2004 | Thieblin et al. | 210/627 |
| 7,001,520 B2 | 2/2006 | Held et al. | 210/609 |
| 7,241,587 B2 * | 7/2007 | Dodge et al. | 435/41 |
| 2005/0040103 A1 | 2/2005 | Abu-Orf et al. | 210/603 |
| 2006/0118485 A1 | 6/2006 | Gallagher et al. | 210/609 |

OTHER PUBLICATIONS

Matias et al., Biotechnology Letters vol. 25, pp. 1351-1356 (2003).*

Koners et al., "Application of the Pulsed Electric Field Treatment . . . ", presentation at a conference in Europe, Sep. 20, 2004, pp. 1-6.

(U.S. Govt. publication) "Kinetics of Microbial Inactivation for Alternative Food Processing . . . ", U.S. Food and Drug Administration . . . , Jun. 2, 2000, pp. 1-3.

James M. Jay, Modern Food Microbiology, pp. 190-200, Aspen Publishers, Gaithersburg, MD, 2000.

Chu et al., "Electroporation for the Efficient Transfection of . . . ", Nucleic Acids Research, vol. 15, No. 3, pp. 1311-1325, 1987.

L.R. Beuchat, "Injury and Repair of Gram-Negative Bacteria . . . ", Advances in Applied Microbiology, vol. 23, pp. 219-243, 1978.

J. Baron, "Repair of Wastewater Microorganisms After . . . " (abstract), Water Environ. Res., vol. 69, No. 5, pp. 992-998, 1997.

M. Du Preez, "The Extent of Bacterial Injury After Chlorination . . . " (abstract), Specialized Conference on Disinfection . . . , Kruger Natl. Pk., S. Africa, 1994.

M. Du Preez, "Investigation of Injury of Coliforms After Chlorination" (abstract), Water Sci. Technol., vol. 31, No. 5-6, p. 114(4), 1995.

S.I. Terzieva, "Survival and Injury of *Escherichia Coli* . . ." (abstract), Canadian Journal of Microbiology, vol. 37, No. 10, pp. 785-790, 1991.

Wei et al., "Minimization of Excess Sludge Production . . . ", Water Research, vol. 37, issue 18, pp. 4453-4467 (2003).

* cited by examiner

*Primary Examiner*—James S Ketter
(74) *Attorney, Agent, or Firm*—MacMillan, Sobanski & Todd, LLC

(57) ABSTRACT

A method of treating biocells includes the steps of: a. providing biocells; b. applying at least one stressor to the biocells sufficient to cause nonlethal and reparable cell wall damage to the biocells, thereby putting the biocells in a catabolic state during which catabolic metabolic functions predominate over anabolic metabolic functions; and c. obtaining at least one product produced by the biocells during the catabolic state. In another embodiment, the method includes the steps of: a. providing biocells that are mammalian cells; b. applying at least one stressor to the biocells sufficient to cause nonlethal and reparable cell wall damage to the biocells, the reparable cell wall damage comprising openings that allow increased passage of materials through the cells walls; and c. inserting foreign DNA through the openings into the biocells.

13 Claims, 4 Drawing Sheets

METHOD OF TREATING BIOCELLS

CROSS-REFERENCE TO RELATED APPLICATION

This application claims the benefit of U.S. provisional application Ser. No. 60/718,667 filed on Sep. 20, 2005.

BACKGROUND OF THE INVENTION

1. Field of the Invention

This invention relates generally to effecting reparable damage to biological cells and microorganisms (collectively, biocells), particularly to promote catabolic metabolic functions over anabolic metabolic functions. More particularly, this invention relates to providing sub-lethal injury to biocells, whereby the biocells retain sufficient vitality to repair themselves and, thus, maintain viability. Even more particularly, this invention relates to providing such sub-lethal injury to biocells, whereby their catabolic metabolic functions predominate over their anabolic metabolic functions and biocell maintenance is maximized and multiplication is minimized. Further, this invention relates to reparable biocell damage for release and recovery of useful cell products. Further, this invention relates to reparable cell damage resulting in increased cell wall conductivity, to allow insertion of foreign substances such as DNA effecting recombinant DNA applications without significant cell death.

2. Description of Related Art

In conventional biological wastewater treatment (WWT) facilities, large amounts of excess biomass (sludge) are produced as by-products. It is desirable, however, to minimize excess sludge production which is effected by applying various treatments such as thermal, electrical, oxidative, or chemical to the biological process. Conventional methods generally employ application of high-energy to irreparably damage the biocells. Such treatment methods involve high energy levels effected by high intensities, longer treatment times, and/or a larger number of treatments.

Abu-Orf et al. (U.S. Pat. Pub. No. 2005/0040103) discloses the use of directed energy (mechanical or hydraulic shear or ultrasonic energy) delivered to a recycle, or recirculation, stream of an anaerobic digester to break sludge floc, or aggregates thereof, solubilize or promote solubility of organic matter, or lyse cells. Similarly, U.S. Pat. No. 6,402,065 to Higgins discloses the use of cavitation and impingement in a so-called dispersion mill.

U.S. Pat. Nos. 6,030,538 and 6,395,176 to Held et al. disclose the use of pulsed-electric field (PEF) effect including an electric field in excess of 15 to about 100 kV/cm and energy in the range of 32-135 J/ml to rupture cell membranes to remove water content. As disclosed, the application of this level of voltage causes "irreparabl[e] rupturing [of] the membranes of the cellular units" and "massive disruption to the cellular matter as well as the release of bound and intracellular liquids". Specifically, test results disclosed in the '538 patent indicate that PEF of 6-7.5 kV/cm for 40 pulses delivered an insufficient energy level of 78-135 J/ml to achieve the desired cellular event. Other related patents by Held et al. are U.S. Pat. Nos. 6,491,820; 6,540,919; 6,709,594 and 7,001,520. All of these Held et al. patents are incorporated by reference herein.

Similarly, U.S. Pat. No. 6,039,867 to Frei et al. discloses exposing sludge to sonic radiation in the area of 500-1,500 W/m$^2$ in order to split the cell walls and U.S. Pat. No. 5,380,445 to Rivard et al. discloses the use of sonic and shear force energy to break cells and disrupt organic matter.

Wei et al., in "Minimization of excess sludge production for biological wastewater treatment" (37 *Water Research* 4453-4467 (November 2003)), disclose that micro-organisms may be just damaged to the point where energy produced in catabolic reactions is driven toward maintenance and reparation functions, as opposed to biomass production. In "Fish Processing by the Elsteril Process", Krupp, *Brochure Krupp Maschinentechnik GmbH*, Hamburg, Germany (1988) is an explanation of lethal effect of strong electric fields on biological cells according to the "dielectric rupture theory". As described therein, the cell membrane, when exposed to an electric field equal to, or slightly above, a Critical Electric Field Intensity forms reparable pores. When the Critical Electric Field Strength is greatly exceeded, the pores become irreparable and the cell membranes are destroyed, resulting in cell death. This latter phenomena is the traditional method for biological WWT to reduce biosludge. Finally, "Kinetics of Microbial Inactivation for Alternative Food Processing Technologies—Pulsed Electric Fields", U.S. Food and Drug Administration Center for Food Safety and Applied Nutrition (Jun. 2, 2000) discusses the concept of a time constant associated with electrical breakdown in the context of non-thermal food preservation.

BRIEF SUMMARY OF THE INVENTION

The invention relates to a method of treating biocells. The method comprises the steps of: a. providing biocells; b. applying at least one stressor to the biocells sufficient to cause nonlethal and reparable cell wall damage to the biocells, thereby putting the biocells in a catabolic state during which catabolic metabolic functions predominate over anabolic metabolic functions; and c. obtaining at least one product produced by the biocells during the catabolic state.

In another embodiment, the method comprises the steps of: a. providing biocells; b. applying at least one stressor to the biocells sufficient to cause nonlethal and reparable cell wall damage to the biocells, thereby putting the biocells in a catabolic state during which catabolic metabolic functions predominate over anabolic metabolic functions; c. in a first collection step, collecting for use at least one first product produced by the biocells during the catabolic state; and d. in a second collection step a period of time after the first collection step, collecting for use at least one second product produced by the biocells during the catabolic state and produced after the first collection step.

In a further embodiment, the method comprises the steps of: a. providing biocells that are mammalian cells; b. applying at least one stressor to the biocells sufficient to cause nonlethal and reparable cell wall damage to the biocells, the reparable cell wall damage comprising openings that allow increased passage of materials through the cells walls; and c. inserting foreign DNA through the openings into the biocells.

BRIEF DESCRIPTION OF THE SEVERAL VIEWS OF THE DRAWINGS

The following detailed description of the embodiments of the invention will be more readily understood when taken in conjunction with the following drawing, wherein.

DETAILED DESCRIPTION OF THE INVENTION

Figure 1:
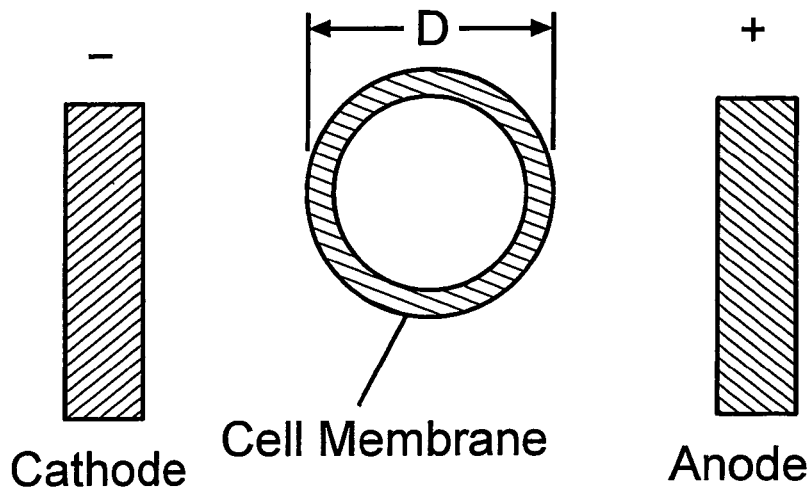
FIG. 1 is pictorial representation of the lethal effect of strong electric fields on biological cells according to the "dielectric rupture" theory of Krupp.
Figure 1:
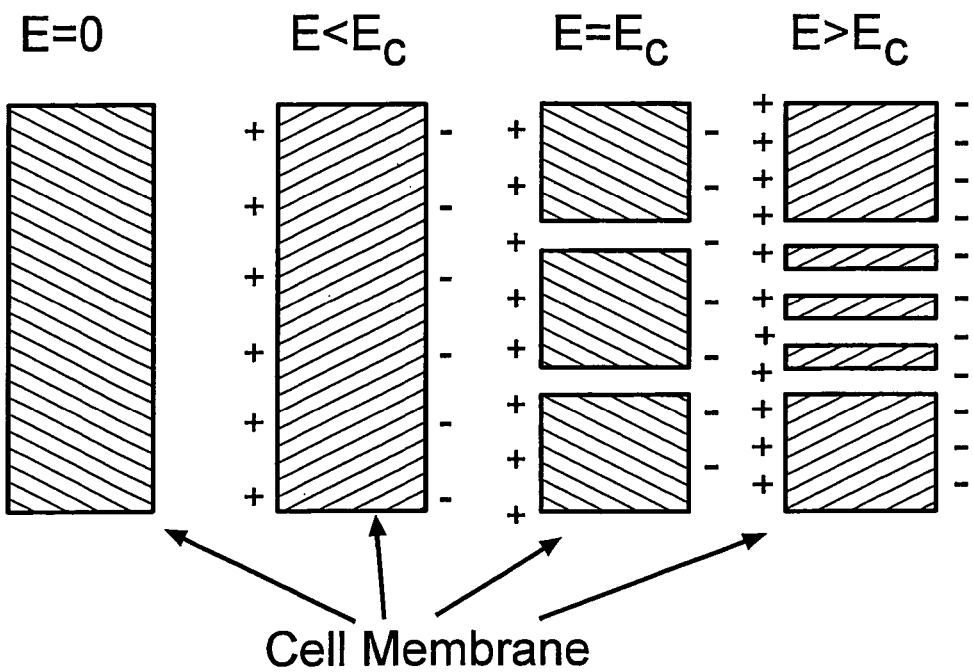

It has been surprisingly and unexpectedly found that the application of one or more of a variety of stressors on biocells, including electric (e.g., PEF), acoustic (e.g., ultrasonic), and magnetic fields, extreme temperatures, radiation (e.g., UV), and chemical treatment (e.g., extreme pH, oxidation, disinfectants, and chemolyzers) at such levels that the cell walls of the biocells are reparably damaged, but not irreparably destroyed/lysed, can lead, for example, to reduced biosludge accumulation. In addition, the technique of the present invention is applicable to harvesting desirable products being produced within the walls of the biocells. In practice, the basic functions of the biocells to metabolize food is continued (and the bioreactor operation sustained) with the associated energy directed primarily to cell repair (catabolic metabolism) rather than cell proliferation (anabolic metabolism). As used herein, the term "catabolic state" refers to the condition of the biocells between the time that their cell walls have been reparably damaged and the time that the damage has been fully repaired by the biocells. This result is effected by operating conditions quite different from those causing the irreparable damage noted above. The growth or yield of the biocells is reduced during the catabolic state. Preferably, the growth is reduced by at least about 50% compared to the same biocells in the same environment without the application of the stressor, and more preferably at least about 75%. The growth is reduced during at least a portion of the catabolic state, and preferably during the majority of the catabolic state.

The reparable cell wall damage of the biocells can take many different forms. In one embodiment, the reparable cell wall damage causes increased conductivity of the cell walls. For example, the reparable cell wall damage may take the form of openings in the cell walls that allow increased passage or transmission of material(s) through the cell walls. The openings can be any type that allow increased conductivity, such as pores, tears, perforations, or the like, or combinations thereof. Any suitable materials may be transmitted through the openings in the cell walls. For example, the material may be a fluid or a solution or suspension of material(s) in a fluid.

At least a portion of the biocells in a bioreactor are subjected to reparable cell wall damage. Preferably, a majority of the biocells are subjected to reparable cell wall damage, and more preferably at least about 75% of the biocells. In one particular embodiment, a PEF process applies a pulsed electric field of between about 2 kV/cm and less than 15 kV/cm, treatment times of between 5 microseconds for a higher field and 20 microseconds for a lower field with each electric field pulse lasting about 0.2 microseconds to about 5 microseconds. Total energy input is between about 1 and 10 J/ml. While in cases of spores or hard-to-damage organisms, it may be necessary to employ field strengths of 15 kV/cm or greater, treatment duration and energy input are kept at minimal levels to avoid irreparable damage. As will be appreciated by those skilled in the art, the bioreactor may include, for example biodegradation or biosynthesis.

In another particular embodiment, at least a portion of the biocells are exposed to an ultrasonic treatment operating below about 500 W/cm$^2$ for shorter times than conventional lysing treatments, whereby cavitation is avoided but at least a portion of the treated biocells are reparably damaged.

FIG. 1 illustrates the effects of strong electric fields on biological cells as described by Krupp (1988) and others, notably, Mertens and Knorr in "Developments of Nonthermal Processes for Food Preservation", *Food Technology* (May 1992). High electric field pulses rely upon the lethal effect of strong electric fields for the inactivation of micro-organisms. In the so-called dielectric field rupture theory, the external electric field induces an electric potential over the cell membrane, which, in turn, causes a charge separation in the membrane. When the transmembrane potential exceeds a critical value, $E_C$, the repulsion between charge-carrying molecules causes the formation of pores in the cell membrane. At this stage of the process, the pores are reparable so that the damage to the cells is reparable. However, when the transmembrane potential is greatly exceeded, the pores become irreparable, the cell membranes are destroyed, and the cell dies/lyses.

Figure 2:
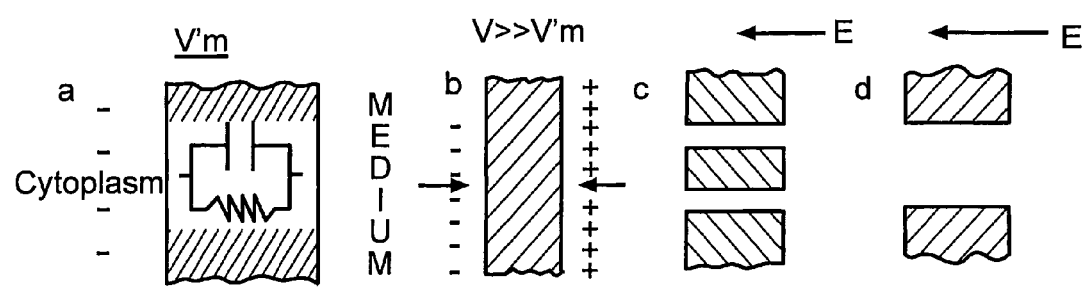
FIG. 2 is a pictorial representation of electrical breakdown of cell membranes according to Zimmerman as described in "Kinetics of Microbial Inactivation for Alternative Food Processing Technologies—Pulsed Electric Fields", U.S. Food and Drug Administration Center for Food Safety and Applied Nutrition (Jun. 2, 2000).

FIG. 2 illustrates the capacitor theory of cell breakdown according to Zimmermann (1986) in which the membrane can be considered as a capacitor file with a dielectric. The normal resisting potential difference across the membrane V'm is 10 mV and leads to the build-up of a membrane potential difference V due to charge separation across the membrane. V is proportional to the field strength E and radius of the cell (FIG. 1). The increase in membrane potential leads to a reduction in the cell membrane thickness. Breakdown of the membrane causing the formation of pores in the membrane occurs if the critical breakdown voltage $V_C$ is reached by further increase in the external field strength. At this stage of the process, the pores are relatively small in size and number so that the membrane is still reparable. However, above critical field strengths, and with long exposure times, larger areas of the membrane are subjected to breakdown. If the size and number of pores become large in relation to the total membrane surface, irreparable breakdown occurs.

Figure 3:
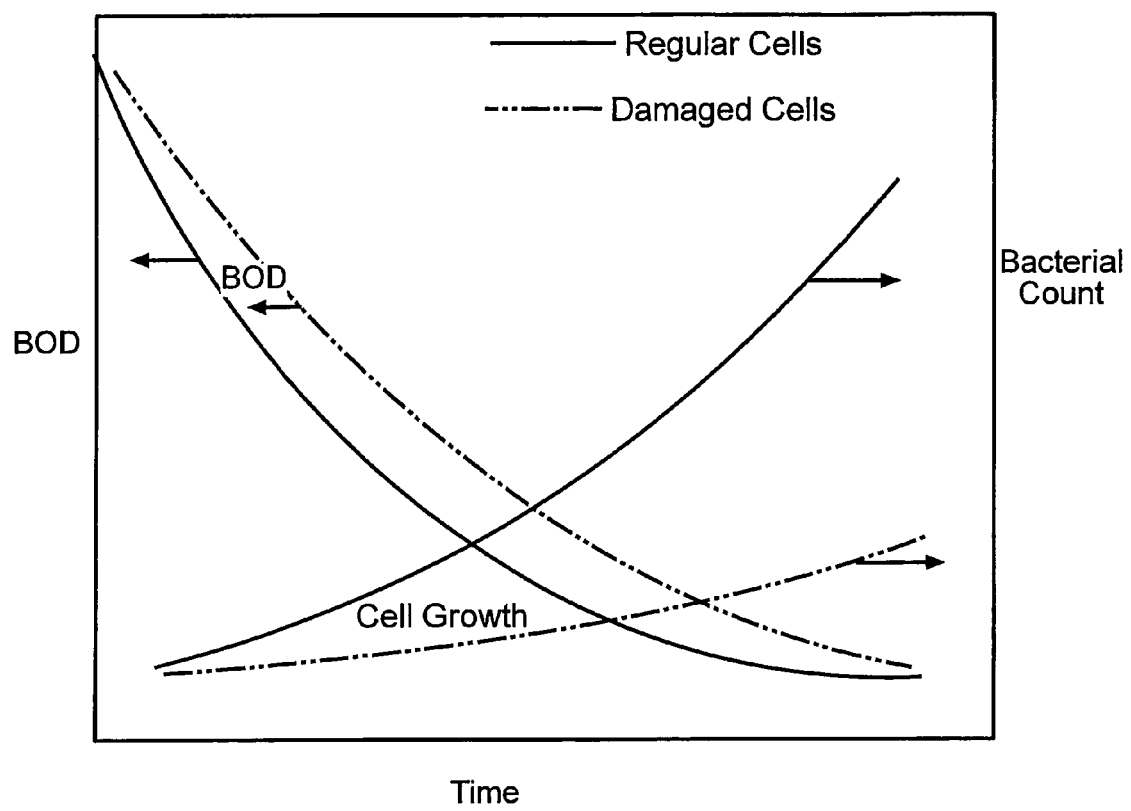
FIG. 3 is a conceptual diagram for reparable damage of bioreactor cells to reduce cell yield.

FIG. 3 illustrates the effect of cell damage on BOD (biochemical oxygen demand) and Bacterial Count. The BOD represents the substrate (food) for the microorganisms (cells). When the BOD is introduced to a cell population, the BOD is consumed by the cells metabolizing the BOD. The BOD is converted to new cells (anabolism) and converted to simpler substances, with energy release (catabolism). The amount of cell production with BOD consumption is known as the cell yield, normally expressed as mass of cells produced per mass of BOD (substrate) consumed. In unstressed (regular) cell production, the cell propagation by conversion of the BOD to new cell mass is significant. However, when cells are stressed to cause reparable damage to the cell walls, there is a shift in the metabolic ratio of catabolism and anabolism, in that the cells utilize the substrate for overcoming the stress by repairing the cell walls, and more catabolic activity occurs. This results in lower anabolism or lower cell growth. In other words, for damaged cells, the cells will use the substrate (BOD) to repair the damage, and the propagation of new cells will be decreased.

As shown in FIG. 3, cell growth is substantially reduced in the Damaged Cells case versus the Regular Cells case. The rate of utilization of the BOD may decrease to some extent for the Damaged Cells, but BOD can be reduced to the same extent as the Regular Cells.

Figure 4:
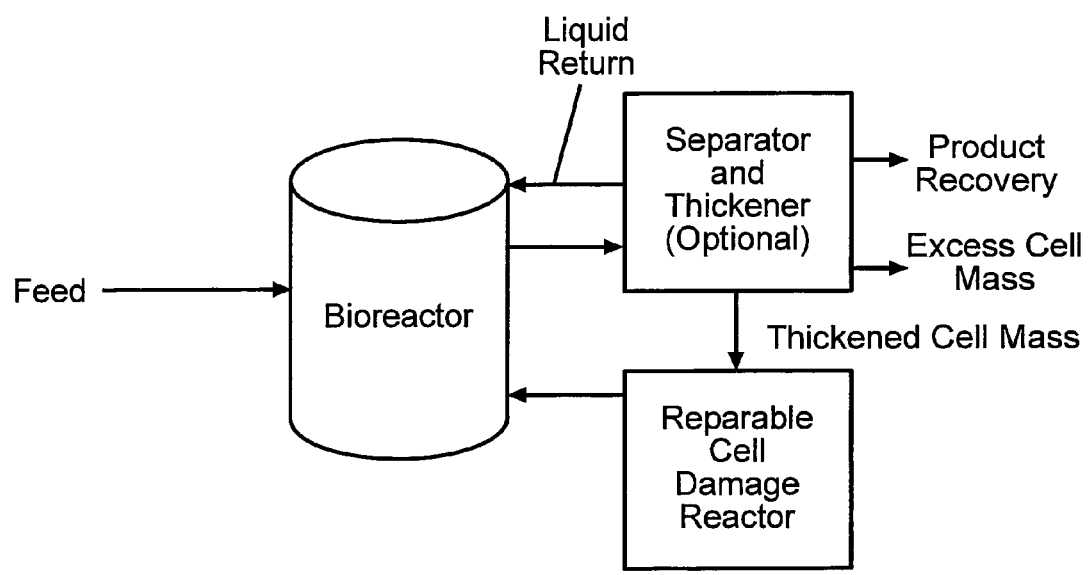
FIG. 4 is a block diagram of a process according to the present invention.

FIG. 4 is a block diagram of a treatment process according to the present invention. A biological reactor (bioreactor) receives a feedstock material for processing. The feed contains biocells and it may contain nutrients, raw materials for processing, and/or contaminants. After the bioreactor processing is complete (batch or continuous flow), the effluent of the reactor is sent to a separator for cell separation and product recovery. The separated excess cell mass (sludge) is sent for further processing and/or disposal; the amount of excess cell mass is decreased in this process. The biomass remaining in the separator may be optionally further thickened to reduce the cell treatment volume and, thus, treatment costs. The liquid from the optional thickening is returned to the bioreactor or further processing for product recovery or treatment.

The separated and optionally thickened biosolids are sent to a reparable cell damage reactor for treatment according to the present invention. The reparably damaged cells are then returned to the bioreactor to provide the active biomass for feedstock processing. The objective is to return the bulk of the biomass as damaged cells, rather than destroying/killing the cells in the cell treatment reactor. Thus, instead of the cell mass being irreparably damaged to effect digestion in a suitable digester, the bulk of the biocells in the bioreactor receive controlled, reparable damage treatment. The biocells are damaged but not killed and as a result they keep functioning. Also, much of the energy produced by the cells is used for repairing the cells rather than growing new cells.

The feedstocks may be various chemicals for bioprocessing to commercial end products, with the appropriate nutrients, chemical additives, and solvents for creating the environmental conditions needed for the bioreactor conversion of the feedstock to the end product. The end products can be any type that are capable of being produced by biocells. The invention includes a step of obtaining at least one product produced by the biocells during the catabolic state. The term "obtained", as used herein, includes both applications in which the product is collected and applications in which the product is produced but not collected. Some nonlimiting examples of applications in which the product is collected from the biocells for use include the production of medicinal products, non-medicinal chemical products, and nutritional products. For example, the biocells can be yeast cells that produce any of a variety of fermentation products, such as ethanol. As another example, the biocells can be used as pharmaceutical factories to grow products within the cells that are harvested and made into any of a wide variety of pharmaceutical products. Examples of applications in which the product is produced but not collected include cleaned-up innocuous end products. For example, the feedstock may be a wastewater, and the bioprocess converts the wastewater contaminants into innocuous end products. Biomass production in the system is minimized by utilizing conditions that damage the biomass cells in the process and result in higher levels of catabolic metabolism in the bioreactor.

In some applications, the reparable damage caused by the method of the invention can be used to achieve additional benefits. For example, the reparable damage may allow a product to be collected from the biocells and then, after the passage of time, additional product to be collected. In one embodiment, the reparable damage is in the form of pores or other openings in the membranes of the biocells. The openings can allow the product to be collected without having to rupture the membrane and thereby kill the biocell in order to gain access to the interior of the biocell. For example, the product may be excreted or pulled through the openings and collected extracellularly. After the collection of the product, the biocell retains is viability so that it can produce additional product. After a period of time, this newly produced product can also be collected. In some embodiments this may be repeated multiple times.

In another embodiment, the invention relates to a method of treating biocells comprising the steps of: a. providing biocells that are mammalian cells (e.g., by extracting biocells from a mammalian organism and culturing the biocells); b. applying at least one stressor to the biocells sufficient to cause nonlethal and reparable cell wall damage to the biocells, the reparable cell wall damage comprising openings that allow increased passage of materials through the cells walls; and c. inserting foreign DNA through the openings into the biocells. In a particular embodiment, the method includes the further steps of: d. allowing the biocells to repair the cell wall damage; and e. inserting the repaired biocells into a mammalian organism to effect recombinant DNA therapy (gene therapy).

There are a number of techniques that have been tested for transinfection of DNA into eukaryotic cells, taken from organisms, for inserting desired genes. Typically most of these techniques are inefficient in terms of amount of DNA matter inserted as well as mortality of cells. The use of electroporation, achieved with the use of an electric field, has been researched previously (see "Electroporation for the efficient transinfection of mammalian cells with DNA", Gilbert Chu, et. al; Nucleic Acids Research; Vol 15, Number 3, 1987). While these electroporation tests were successful in inserting the DNA, the cell mortality was too high even at the low electric field (0.53 kV/cm) that was used. The reason for this "irreversible cell damage" is the long treatment time (500 to 7,000 microseconds) employed. In the invention reported here, the treatment time is about two orders of magnitude lower and treatment is controlled by—using electric field pulses of a short duration, so somewhat higher fields can be employed. Additionally, techniques other than pulsed electric field may be used for repairable cell wall disruption to allow DNA insertion, followed by cell repair through culturing; this is then followed by delivery of the transinfected cells to an organism to effect recombinant DNA therapy.

While the invention has been described in connection with specific embodiments as shown and described, it is to be understood that numerous changes and modifications may be made therein without departing from the scope and spirit of the invention as set forth in the appended claims.

The invention claimed is:

1. A method of treating biocells comprising the steps of:
   a. providing biocells;
   b. applying at least one stressor to the biocells sufficient to cause nonlethal and reparable cell wall damage to the biocells, thereby putting the biocells in a catabolic state during which catabolic metabolic functions predominate over anabolic metabolic functions; and
   c. obtaining at least one product produced by the biocells during the catabolic state, wherein the stressor is a pulsed electric field of between 2 kV/cm to less than 15 kV/cm, applied for between 5 and 20 microseconds, with each electric field pulse lasting about 0.2 to about 5 microseconds, at a total energy input of between about 1 to 10 J/ml.

2. The method of claim 1, wherein the reparable cell wall damage causes increased conductivity of the cell walls.

3. The method of claim 2, wherein the reparable cell wall damage comprises openings that allow increased passage of materials through the cell walls.

4. The method of claim 1, wherein the product is collected from the biocells for use.

5. The method of claim 1, wherein the product is selected from the group consisting of medicinal products, non-medicinal chemical products, nutritional products, and wastewater end products.

6. The method of claim 1, wherein biocell growth during the catabolic state is reduced by at least about 50% compared to the same biocells in the same environment without the energy application.

7. The method of claim 6, wherein the biocell growth is reduced by at least about 75%.

8. The method of claim 1, wherein the stressor for causing cell wall damage is a pulsed electric field.

9. The method of claim 1, wherein the stressor for causing cell wall damage is electrical energy which is equal to $E_C$.

10. A method of treating biocells comprising the steps of:
   a. providing biocells;
   b. applying at least one stressor to the biocells sufficient to cause nonlethal and reparable cell wall damage to the biocells, thereby putting the biocells in a catabolic state during which catabolic metabolic functions predominate over anabolic metabolic functions;
   c. in a first collection step, collecting for use at least one first product produced by the biocells during the catabolic state; and
   d. in a second collection step a period of time after the first collection step, collecting for use at least one second product produced by the biocells during the catabolic state and produced after the first collection step, wherein the stressor is a pulsed electric field of between 2 kV/cm to less than 15 kV/cm, applied for between 5 and 20 microseconds, with each electric field pulse lasting about 0.2 to about 5 microseconds, at a total energy input of between about 1 to 10 J/ml.

11. The method of claim 10, wherein the stressor application creates reparable openings in biocell membranes that allow the collection of the first product in the first collection step without killing the biocells.

12. The method of claim 11, wherein the first product flows through the pores and is collected extracellularly in the first collection step.

13. The method of claim 10, wherein the product is selected from the group consisting of medicinal products, non-medicinal chemical products, and nutritional products.

* * * * *